(12) United States Patent
Manolas

(10) Patent No.: US 7,107,095 B2
(45) Date of Patent: Sep. 12, 2006

(54) DEVICE FOR AND METHOD OF RAPID NONINVASIVE MEASUREMENT OF PARAMETERS OF DIASTOLIC FUNCTION OF LEFT VENTRICLE AND AUTOMATED EVALUATION OF THE MEASURED PROFILE OF LEFT VENTRICULAR FUNCTION AT REST AND WITH EXERCISE

(76) Inventor: Jan Manolas, Pan. Zervoustr 5, Paleon Psychikon, TT 153 52, Athens (GR)

( * ) Notice: Subject to any disclaimer, the term of this patent is extended or adjusted under 35 U.S.C. 154(b) by 535 days.

(21) Appl. No.: 10/425,315

(22) Filed: Apr. 29, 2003

(65) Prior Publication Data

US 2003/0204145 A1 Oct. 30, 2003

(30) Foreign Application Priority Data

Apr. 30, 2002 (DE) ................................ 102 19 367

(51) Int. Cl.
*A61B 5/02* (2006.01)
*A61B 5/04* (2006.01)
(52) U.S. Cl. ....................... 600/513; 600/508; 600/528
(58) Field of Classification Search ................ 600/481, 600/485, 508, 520, 526, 528
See application file for complete search history.

(56) References Cited

FOREIGN PATENT DOCUMENTS

DE 197 40 931 4/1999

OTHER PUBLICATIONS

"Comparison between Apexcardiographic and Angiographic Indexes of Left Ventricular Performance in Patients with Aortic Incompetence", Manolas, et al., Circulation, vol. 57 No. 4, Apr. 1978 pp. 692-698.

"Usefulness of Noninvasive Detection of Left Ventricular Diastolic Abnormalities During Isometric Stress in Hypertrophic Cardiomyopathy and in Athletes", Manolas et al., American Journal of Cardiology, vol. 81, Feb. 1, 1998, pp. 306-313.

"Indentification of Patients with Coronary Artery Disease by Assessing Diastolic Abnormalities During Isometric Exercise" Manolas, et al., Clin. Cardiol. 24; Nov. 2001:pp. 735-743.

"Noninvasive Evaluation of Progression of Ischemic Heart Disease: 5 Year Follow-Up", Manolis, J. Acta Cardiologica, vol. XLVII, 1992, pp. 359-366.

"Patterns of Diastolic Abnormalities During Isometric Stress in Patients with Systemic Hypertension", Manolis, J. Cardiology 1997; 88:pp. 36-47.

(Continued)

*Primary Examiner*—Kennedy Schaetzle
*Assistant Examiner*—Yun Haeng Lee
(74) *Attorney, Agent, or Firm*—Katten Muchin Rosenman LLP

(57) ABSTRACT

In a method of noninvasive measurement of parameters of diastolic function of left ventricle and automated evaluation of the measured profile at rest and with exercise, a patient performs an isometric exercise. An external pressure sensor and heart sounds microphone are applied in a non-invasive manner on the thoracic wall to obtain a left ventricular pressure mirroring curve (pressocardiogram) and simultaneously the heart sounds (phonocardiogram). An external unit determines and calculates characteristic diastolic parameters derived from the pressocardiographic curve and phonocardiogram at rest, during and after exercise, converts each said pressocardiogram into a digital waveform in the time domain, and automatically categorizes the mentioned characteristic parameters based on exact categorization criteria for defining several differentialforms of diastolic dysfunction of left ventricle in human beings.

34 Claims, 7 Drawing Sheets

OTHER PUBLICATIONS

"Ischemic and Nonischemic Patterns of Diastolic Abnormalities During Isometric Handgrip Exercise", Manolas, J. Cardiology 1995; 86: pp. 179-188.

"Atrial Function can only be Assessed by Combined Use of Volume- and Pressure-Assessing Noninvasive Method" Manolas, J., JACC vol. 25, No. 2; Feb. 1995; 2 Pages.

"Comparison of Handgrip- Apexcardiographic Test and Stress-ECG for Identifying Patients with Coronary Artery Disease" Manolas, J., Herz 18: 1993, pp. 256-266.

"Noninvasive Detection of Coronary Artery Disease by Assessing Diastolic Abnormalities During Low Isometric Exercise", Manolas, J., Clin. Cardiol. 16: 1993; pp. 205-212.

"Value of Handgrip-Apexcardiographic Test for the Detection of Early Left Ventricular Dysfunction in Patients with Angina Pectoris", Manolas, J., Z Kardiol 79: 1990; pp. 825-830.

"Filling Patterns During Isometric Stress by Handgrip Exercise" Manolas, J., Heartforum Suppl 1-1997; vol. 10 The First Diastology Meeting, Nov. 28-30, 1996: pp. 28-31.

"Diastolic Amplitude Time Index: A New Apexcardiographic Index of Left Ventricular Diastolic Function in Human Beings" Manolas, et al., The American Journal of Cardiology, vol. 48 Oct. 1981; pp. 736-745.

"Use of Apexcardiography to Evaluate Left Ventricular Diastolic Compliance in Human Beings", Manolas et al., The American Journal of Cardiology, vol. 43; May 1979, pp. 939-945.

"Relation Between Apex Cardiographic and Internal Indices of Left Ventricular Relaxation in Man", Manolas, et al. British Heart Journal, vol. 39 (XXXIX), No. 12, Dec. 1977: pp. 1324-1332.

"Time Relation Between Apex Cardiogram and Left Ventricular Events Using Simultaneous High-Fidelity Tracings in Man" Manolas, et al., British Heart Journal, vol. 37 (XXXVII), No. 12 Dec. 1975: pp. 1263-1267.

DEVICE FOR AND METHOD OF RAPID NONINVASIVE MEASUREMENT OF PARAMETERS OF DIASTOLIC FUNCTION OF LEFT VENTRICLE AND AUTOMATED EVALUATION OF THE MEASURED PROFILE OF LEFT VENTRICULAR FUNCTION AT REST AND WITH EXERCISE

FIELD OF THE INVENTION

This invention is in the cardiology and relates to the detection of heart dysfunction by use of pressocardiographic test in human beings. The so-called pressocardiograms are obtained from the chest wall by a pressure transducer in order to detect left ventricular (LV) diastolic dysfunction at rest and during short exercise. Specifically, this invention consists in a device—ideally portable and in pocket form— for assessing and calculating diastolic LV function indices as well as for evaluating the test results and above in differentiating characteristic patterns and differentialforms of diastolic behavior with exercise.

BACKGROUND OF THE INVENTION

Previous attempts to obtain high-fidelity tracings from the point of maximal pulse of the heart beat—referred as apexcardiography—have been handicapped mainly because of lack of an advanced instrumentation and automated evaluation of exactly defined diastolic indices as well as of exactly defined patterns, types and forms of isometric exercise-induced changes in diastolic profile.

Pressocardiography represents the only noninvasive technique which is obtained by means of an external pressure transducer transthoracically, providing the opportunity to measure LV pressure curve changes in diastole at rest and during short isometric exercise (called Handgrip-pressocardiographic test=HAT) by an operator with minimal medical skills.

This diastolic stress test HAT presents the opportunity to measure diastolic performance of the human left ventricle and detect life-threatening abnormal heart conditions in an early phase before development of symptoms or ECG or other signs of myocardial disease states and especially coronary artery disease.

Conclusive evidence exists based predominantly in comparison of simultaneously recorder pressocardiographic and LV pressure curves during heart catheterization that the former mirrors in time and slope the latter. It is widely accepted that invasively obtained LV pressure curves by means of micromanometer represent still today the gold standard for examining the accuracy of diastolic function assessment. The most common diastolic indices which are assessed by means of such high-fidelity LV pressure recordings are the calculation of LV pressure fall (=relaxation) variables, like time constant of relaxation (Tau) and the total LV relaxation time, and end-diastolic variables, like LV end-diastolic pressure, pre-atrial or pre-A wave as well as peak atrial pressures.

On the other hand, current methods of measuring diastolic LV function are either extremely invasive or/and costly or/and noninvasively imaging approaches that require expertise and time-consuming measurements by highly skilled operators. Examples of the former invasive techniques are left and right heart catheterization with subsequent angiographic evaluation (coronary angiography and ventriculography) as well as nuclear ventriculography. An example of the latter are all Doppler echocardiographic techniques providing ultrasonic dynamic images of the heart like transmitral flow velocities, pulmonary venous flow assessment, acoustic quantification, flow propagation assessment and the most recently introduced Tissue Doppler Imaging (TDI) and Strain-Rate Imaging (SRI); however, all these Doppler techniques require highly and expensively developed laboratories as well as skilled interpretation, whereas in most cases there is a lack of exact definition of normal limits and/or of standardization.

Consequently, there was hitherto a lack to assess LV diastolic function alterations, accurately as well as noninvasively, rapidly and safely; and above no simple and at best portable instrumentation—at best in pocket size—using an external pressure transducer with infinite time constant.

In contrast, with the present invention using the diastolic exercise test by means of handgrip-pressocardiography and a portable—at best pocket-sized—instrument, a rapid estimation of diastolic LV function can be performed quickly and noninvasively everywhere, i.e. at every office, at outpatient clinic (incl. CPUs) and even at patient's home, with no requirement of skilled interpretation both at rest and during isometric exercise. A simple readout can provide exact information about early and late diastolic abnormalities within few minutes.

It has been shown using micromanometer measurements and internal LV pressure recordings that the changes of some diastolic variables during isometric handgrip exercise, especially at the end-diastole, is rather characteristic for the presence of some myocardial disease states. Whereas patients with normal or nearly normal LV function show no or only minimal diastolic changes during isometric exercise, patients with coronary artery disease show mostly dramatic alterations and particularly rise in LV end-diastolic pressure. It should be noted that this rapidly occurring and high elevation of LV end-diastolic pressure is also present during other exercise modalities like dynamic exercise by means of bicycle or treadmill.

The inventor has found for the first time that a very similar dramatic changes in early and/or late diastole during isometric exercise occur also using the handgrip-pressocardiography technique in patients with known or subsequently proved coronary artery disease, whereas healthy subjects show no or minimal changes within exactly defined normal limits. Thus, it appears that changes in pressocardiographic curve are also during handgrip exercise unidirectional and similar to those found internally in LV pressure curve during catheterization; the former corresponding the latter.

It was realized by the inventor for the first time that these significant diastolic alterations during exercise-induced ischemia represent a characteristic sign which was called an "ischemic diastolic response" of pressure tracings recorded either invasively or noninvasively. It should be also noted that the corresponding volumetric measurements are less dramatic having a minor magnitude.

The diagnosis of coronary artery disease or other myocardial diseases based on symptoms is not accurate enough, since these symptoms occur rather late in the course of most myocardial diseases and atypical and above not infrequently entirely absent. Alternatively, ECG and systolic abnormalities are usually preceding the onset of symptoms; whereas diastolic dysfunction represents the earliest manifestation in the course of most myocardial diseases.

Conclusive evidence exists that the earliest manifestation of ischemia is diastolic dysfunction—relaxation and end-diastolic abnormalities, preceding both the ECG and the systolic abnormalities on the onset of every ischemic episode. It has been proved in human beings that during ischemia induced by occlusion of a coronary vessel during angioplasty in the left anterior coronary vessel, an extreme prolongation of total relaxation time of the left ventricle occurs within few seconds and is followed after 15–25 sec by a dramatic rise in LV end-diastolic and left atrial pressures which are reaching a more than 150% of the base line values.

Based on heart catheterization data and high-fidelity LV pressure curve using micromanometers and exact early (relaxation) and late (end-diastolic and left atrial pressures) measurements, it has further been shown that diastolic abnormalities as assessed by LV pressure curve measurements are much more pronounced than volumetric abnormalities in diastole or systole (including left ventricular ejection fraction).

Therefore, it appears that the assessment of LV pressure curve in diastolic phase in everyday practice at rest and during short exercise could be of fundamental clinical importance. Further, it is also logical to assume that an instrumentation assessing these early occurring latent exercise-inducible diastolic abnormalities, could represent a very useful diagnostic tool for an early detection of LV dysfunction due to ischemic or other myocardial diseases.

Further, it is also expected that the application of a simple small and user friendly device—at best portable and in pocket size—for obtaining a "diastolic stress test" assessing the mentioned early and late LV pressure curve changes in everyday practice, would be a very useful daily tool leading us probably to an earlier identification of patients with subclinic CAD before the onset of symptoms or systolic dysfunction (assessed by echocardiogram) or electrical changes (in ECG).

The wide application of such instrumentation would probably result in an improved secondary prevention since it would lead us to an earlier onset of preventive and/or therapeutic strategies.

Most importantly, an isometric handgrip exercise of 2 min duration represents a low level stress to the human left ventricle and all alterations are quickly reversible. In addition, this quick and slight handgrip exercise can be performed on the bed using the one hand. Consequently, this stress test can be widely applied, independently from physical ability, age and health state; i.e. also in disabled and extreme obese persons.

Before the introduction of handgrip-pressocardiography, there was no other simple (needing no expertise and skilled interpretation), noninvasive, quick (procedure of <10 min duration) and safe (no serious complications including myocardial infarction and deaths) as well convenient for all patients diagnostic modality suitable to be applied as screening test for myocardial diseases—including coronary artery disease—even in the earliest subclinic stage.

The probably greatest problem in cardiology but also in health care is still the early identification of subclinic myocardial diseases and especially of asymptomatic patients with coronary artery disease.

Most practitioners are still based on the daily application of resting ECG or stress ECG or resting Echocardiography neither of which is sensitive enough for myocardial disease detection—especially in the earliest asymptomatic stage. Alternatively, more sensitive and specific methods such as nuclear (Thallium) imaging or stress echocardiography (including transeosophageal echo) are time-consuming, not completely non-invasive, very costly and require expert interpretation. Further, dynamic exercise or pharmacological stress tests are not convenient and not completely safe for the patients; resulting either to a decreased desire of the patients or even contraindication for performing them. Therefore, these techniques can not be applied very widely and above they are rather excluded for use by primary care physicians.

This lack of appropriate, accurate and easy applicable techniques for screening healthy looking and feeling patients for "silent myocardial disease states, results in a great still unsolved problem in health care; namely, there are still today yearly >220.000 patients in US dying suddenly due to silent myocardial disease remaining mostly unidentified prior to their sudden death. The underlying disease was in >70% of these cases asymptomatic coronary artery disease and in younger population in >30% undiagnosed "silent" cardiomyopathies.

It should also be emphasized that usually healthy feeling and looking patients in early and sometimes even more advanced stages of myocardial disease, are not coming to the great or university hospitals or at the office of cardiologists in order to be examined by means of the mentioned more sophisticated diagnostic techniques. Thus, these asymptomatic patients suffering on subclinic myocardial disease could only being diagnosed by primary care physicians who, however, do not have enough diagnostic tools for such a screening. In this context, it should be again noted that electrical (resting and stress ECG) and anatomic changes as well as systolic abnormalities (in resting echocardiogram) are all occurring mostly much later in the course of myocardial disease.

A wider application of diastolic tools as diagnostic modalities of early myocardial function alterations appear to represent an alternative useful approach. The classical diastolic tools which are widely accepted for detecting LV diastolic dysfunction are Doppler-echocardiographic and nuclear techniques as well as more recently magnetic resonance imaging techniques. All of them have one or more of the following limitations: they are time-consuming, costly, not standardized and require expert interpretation. Thus, they can not be applied by primary care physicians. In addition, although the gold standard of assessing LV diastolic function are still the internally derived LV pressure curve measurements, all of the mentioned current diastolic techniques are assessing the volumetric filling profile—and this only at rest—and none is using a pressure transducer.

Because of all these limitations and disadvantages, one should conclude that although there is no doubt about the existing and significantly increasing interest on and the clinical importance of diastolic function assessment, the clinical application of diastolic techniques in the daily practice remains rather limited.

In contrast, a HAT detection of subclinic myocardial disease can be accomplished easily, quickly, safely and conveniently with a high sensitivity and specificity in almost every patient and with a simple read out rather than expert interpretation, with the present invention. Most importantly, this diastolic stress test can be performed everywhere by a portable or even pocket sized instrument.

Previous attempts at obtaining and evaluating (apex) pressocardiographic waveforms have been handicapped by the lack of advanced instrumentation, signal processing and pattern recognition techniques. The pulse transducers which have been used had a mostly unknown or too low time constant (<3 sec) using an AC input and piezoelectric recording systems with air transmission by means of air filled tubes. Moreover, they were obtained only at rest and/or after dynamic exercise, whereas the diastolic waves could not be exactly evaluated due to too high heart rate. Both amplitude and above relaxation time indices are greatly influenced by the mode of pick up device and time constant of the pressure transducer. In past years, air-filled tubes were used for transmission of the pulse signal and transducers with too short time constant resulting in distorted tracings.

These earliest versions of "displacement cardiography" were designed as ballistocardiography and kinetocardiography being rather qualitatively than quantitatively evaluated and mostly also in relation to the phonocardiographic recordings. All these tracings as well as carotid pulse and jugular vein recordings have been used for many years in the daily practice as routine tools being termed mechanocardiography. Out of all these earlier developments only arterial pulse recordings have survived which have began recently to be reevaluated as "arterial pulse wave" tracings for evaluating arterial pulse wave velocity and arterial elasticity or compliance, which is again receiving widespread acceptance.

The (apex)cardiography has been primarily used for an improved interpretation of heart sound and murmurs. However, already in earlier years the significance of measuring the relative A wave amplitude and less also of the relaxation time of the "apex tracing". Using for the first time simultaneously external and internal pressure transducers with infinite time constant for obtaining high-fidelity tracings during heart catheterization, Jan Manolas and other cardiologists in University of Zurich, proved for the first time in human beings the significant correlation between relative A wave indices and total Relaxation time indices of the external pressure curves with the corresponding LV end-diastolic pressure and relaxation speed indices derived internally from the LV pressure curve (Ref. 3).

The Handgrip-pressocardiographic Test (HAT) has been introduced and first published in 1990 and further developed till today by Dr. Jan Manolas. The present inventor has recognized that the technology for clinical application requires an exact definition of normal limits of the diastolic indices of LV function and a positive-negative diagnosis of the presence of myocardial dysfunction and underlying myocardial disease as well as an assessment of the severity of this functional abnormality. Additionally, the inventor also recognized that by introducing an exact definition of the profile of handgrip-induced changes of the diastolic variables, one can easily discriminate among different diastolic behavior patterns.

The aim of this diastolic stress test is to assess the level of some diastolic variables corresponding to analogous diastolic function indices derived from left ventricular (LV) pressure curve as well as changes of these parameters with exercise, exploring its usefulness as an initial screening tool in identifying patients with LV diseases including coronary artery disease.

The HAT technique is obtained by a pressure transducer and mirrors LV pressure curve in time and slope; however, in contrast to the latter it is obtained noninvasively. This stress pressocardiography can be applied safely and in a convenient way in every patient, since it is of short duration and the exercise mode is only a low level isometric handgrip performed by the one hand with the patient being recumbent on the bed. Therefore, this low level stress test can be widely applied, independently from the level of physical ability, age and health state of the patient.

Before the introduction of HAT, there was no other noninvasive, simple (not needing expertise), quick (of <10 min duration), safe (without potential life threatening complications like acute infarction, ventricular tachycardia or deaths), and convenient for the patient and examinator for diagnosing myocardial diseases, including coronary artery disease.

A similar device is for obtaining a HAT is partly reported by DE 197 40 931 C2. This device consists in an external pressure transducer for obtaining noninvasive pressure curves and a balloon dynamometer for allowing the patient to perform an isometric handgrip exercise and a device for calculating diastolic parameters derived from the pressocardiographic curve at rest and during handgrip exercise in order to receive some diagnostic information about the presence or not of early and late diastolic abnormalities.

However, the received information needs a skilled further interpretation by a cardiologist and does not allow a rapid automated cardiac performance and diastolic behavior estimation by every non-expert physician or lab assistant, since an information about differentiation of underlying disease (ischemia vs non-ischemic or hypertensive myocardial disease vs Cardiomyopathy etc.) could not be derived from this previous technology.

As previously described, a device for isometric handgrip exercise by the patient is used, e.g a balloon dynamometer, which should be squeezed at approximately 40% of the maximal voluntary contraction during 2 min. At rest during and after handgrip exercise the following variables are calculated semi-automatically by means of a normalized pressocardiographic and phonocardiographic digital signal:

A/H=the relative A wave height to total systolic-diastolic excursion of pressocardiogram A/D=the relative A wave to total diastolic height of pressocardiogram TART=the Total (Apex)pressocardiographic Time from begin of aortic component of the second heart sound to the protodiastolic nadir of pressocardiographic curve or O point.

TARTI=the Total (Apex)pressocardiographic Relaxation Time Index, which is given by the following formula:

$$TARTI=\sqrt{A2-C}/TART$$

where A2 is the onset of the aortic component of the second heart sound in the phonocardiogram and C the onset of the pressocardiographic systolic upstroke. TARTI represents a modified Bazett formula, which has been used to correct temporal variables for heart rate; whereas the duration of diastolic phase is being used instead of R-R interval.

DATI=the Diastolic Amplitude Time Index, which represents the first attempt to assess by a combined single index the total early and late diastolic function and is given by the following formula:

$$DATI=TARTI/(A/D)$$

Based on the absolute value of these diastolic indices at rest and during exercise, one can receive some diagnostic information. The presence of diastolic dysfunction is estimated by evaluation of a "positive" test result. Further, the presence of early or/and late diastolic abnormalities was evaluated for defining some types of diastolic dysfunction during handgrip exercise. This approach has, however, some significant shortcomings:

1. The mentioned definition of positive/negative and of diastolic types was based on normal limits according to published papers of the present inventor, which were obtained by a transducer having a different time constant from the mentioned new device.
2. Patients without or only borderline myocardial dysfunction showed a "false positive" test result and the definition of different types was incomplete.

3. No exactly defined classification of the severity of LV diastolic dysfunction and myocardial disease could be provided
4. No exactly defined differentiation of underlying myocardial disease with automatic classification of these patients could be provided
5. A positive HAT result & types definition could not help us significantly in decision making (to be admitted or discharged) in cases of atypical unstable angina
6. A positive HAT result & types could not help us greatly in decision about performing a coronary angiography.

This patent application addresses these previous shortcomings and difficulties in automated interpretation of HAT for improving the interpretation and diagnostic power and practically usefulness of this "diastolic stress test" as initial screening tool by providing an improved appropriate device which allows a more rapid automated diastolic performance estimation and myocardial ischemia in a robust manner without the need of physician or other expert interpretation.

The present inventor recognized that the by him introduced HAT technology requires some methodical and instrumental improvements.

A new definition of the positive/negative result and evaluation of types and a revised formulation of exactly defined diastolic patterns & an introduction of diastolic differentialforms for distinguishing between ischemic vs non-ischemic handgrip-induced alterations and hypertensive vs cardiomyopathic vs coronary vs congestive vs advanced, respectively.

The automated interpretation by a portable and at best pocket sized instrument, avoids the necessity of visual and empirical interpretation of the test result by experts, whereas its small size is further enhancing considerably the practical clinical applicability of this simple stress test.

The inventor has recognized that the present state of the art showed some significant limitations preventing a widespread clinical application especially on the level of primary care. There was a limited automated evaluation of the result and above a non-existent separation of patients with various myocardial diseases based on exactly defined patterns and forms of LV diastolic behavior.

Since primary care physicians still do not have any simple and cost-effective diagnostic techniques which could be used as initial screening tools for early identifying and differentiating patients with suspected or unknown subclinic myocardial diseases—including coronary artery disease, there is a continuing intense interest in introducing simple methods and appropriate instrumentation for quick and safe cardiac evaluation by non-experts in daily practice for preventing acute myocardial infarction or sudden death.

SUMMARY OF THE PRESENT INVENTION

The inventor has recognized that the mentioned problem of early detection and potential differentiation of patients with subclinic myocardial disease is still unsolved, since a significant part of patients with either cardiomyopathy or above silent CAD remain unidentified till their first dramatic acute event or even sudden death. It was also recognized that the previously introduced in literature and further developed by the preset inventor HAT technique, requires an improved definition of criteria of positive-negative diagnosis of the presence of myocardial diseases as well as of assessing early and late-diastolic abnormalities (types) and above a separation of ischemic vs non-ischemic patterns and differentialforms, since the prior system (DE 197 40 931 C2) did not provide accurately utilized and full information content from the HAT result. Moreover, a novel categorization by a new computer-based automation of instrumentation for classifying patients according to the severity of the LV diastolic dysfunction as well as for differentiation of diastolic LV behavior in ischemic vs non-ischemic and various differentialdiagnostic forms leading us to an improved and practically important classification of patients with suspected or unknown myocardial diseases and particularly with subclinic or asymptomatic CAD.

The invention provides a method of rapid noninvasive measurement of parameters of diastolic function of left ventricle and automated evaluation of the measured profile of left ventricular function at rest and with exercise, wherein the patient performs an isometric exercise through an external device, wherein an external pressure transducer and heart sounds microphone are applied as noninvasive sensor units on the thoracic wall to obtain a noninvasive left ventricular pressure mirroring curve (pressocardiogram) and simultaneously the heart sounds (phonocardiogram); and wherein an external utilization unit determines and calculates characteristic diastolic parameters derived from the pressocardiographic curve and phonocardiogram at rest, during and after exercise, converts each said pressocardiogram into a digital waveform in the time domain, and automatically categorizes the mentioned characteristic parameters based on exact categorization criteria for defining at least the following differentialforms of diastolic dysfunction of left ventricle in human beings:

a) a diastolic Hypertensive differentialform;
b) a diastolic Coronary differentialform;
c) a diastolic Cardiomyopathic differentialform;
d) a diastolic Congestive differentialform;
e) a diastolic Advanced differentialform.

A new device comprises: an external transthoracically applicable pressure transducer for obtaining a LV pressure mirroring curve, a separately applicable external heart sounds microphone, a device for performing an isometric exercise, a unit for measuring and semi-automatic calculating parameter of early and late diastole derived from the transthoracically recorded left ventricular pressure curve (pressocardiogram), a computer-based automated categorization of "diastolic differentialforms" based on exact definition of the diastolic variables behavior with exercise. For the first time, cardiac patients are classified in one of at least following diastolic differentialforms which are exactly defined with the present invention:

a) a diastolic Hypertensive differentialform;
b) a diastolic Coronary differentialform;
c) a diastolic Cardiomyopathic differentialform;
d) a diastolic Congestive differentialform;
e) a diastolic Advanced differentialform.

The introduction of new definitions and partly new indices as well as this new computer-based automated categorization of HAT result, represents a significant and clinically important improvement of pressocardiography, since the simplicity of the new system is providing a more practical and quicker readout without requirement for skilled interpretation. The invention provides, thus, both a new classification and instrumentation of HAT technique which is more suitable for a wider and more effective initial screening in the primary care. Additionally, this invention could also become a very useful novel diagnostic modality in sports centers for screening athletes for the presence of subclinic or atypical cardiomyopathies as well as in outpatient clinic— including Chest Pain Units (CPUs) for detecting or ruling out the presence of acute ischemia in patients with suspected unstable angina.

Compared to the conventional ECG devices, the application of the mentioned HAT instrumentation is associated with a higher diagnostic accuracy (sensitivity and specificity/normalcy) and cost-effectiveness without being time-consuming.

The inventor has recognized that the needed technology for an easy and not expertise needing application in the daily practice requires an improved computer-based automation of an instrument to produce an automated categorization of the following parameters:
- a) Detection of at least one parameter which is in a range which is defined as abnormal or pathologic;
- b) Discrimination according to the severity of diastolic abnormalities
- c) Discrimination between early and late diastolic abnormalities
- d) Discrimination between ischemic and non-ischemic diastolic reaction with isometric exercise
- e) Discrimination of diastolic differentialforms The classification was based in a combination of various single parameters used as exactly defined criteria of abnormality as well as of some exactly defined behavior patterns—including directional changes—and some additional patient's data.

The present invention offers the possibility for automated discrimination of various degrees of severity of diastolic dysfunction; by evaluating separately early and late diastolic abnormalities and by distinguishing the presence of a slight, moderate or severe diastolic alteration.

A further classification consists in separating early and late diastolic abnormalities by defining the "diastolic types":
- a) Early diastolic abnormality (Relaxation or R-type)
- b) Late diastolic abnormality (Compliance or C-type), and
- c) Both C- and R- types are simultaneously present in one single beat (mixed or RC-type)

More particularly, the present invention is disclosed for discriminating myocardial disease patients with exercise-inducible ischemia from those without inducible ischemia; this separation helping potentially greatly in decision making about admission in the hospital and/or indication for performing a coronary angiography:
- a) An "Ischemic diastolic response" being defined by a significant exercise-induced rise in LV end-diastolic pressure or an analogous increase in the relative A wave/total excursion of the pressocardiogram; this alteration being 20–75% of the baseline value at rest or/and abnormal absolute or relative (heart rate corrected) prolongation of the relaxation time.
- b) A "Non-ischemic" diastolic reaction In a preferred embodiment, the system and the method of the present invention includes a computer-based discrimination of some categories resulting in a disease-specific differentiation of patients with unknown myocardial disease:
- a) An "Hypertensive differentialform" being characterized by only minimal or moderate diastolic abnormalities and slight exercise-induced changes
- b) A "Coronary differentialform" characterized by dramatic exercise-induced magnitude of changes in relaxation and/or relative A wave/total excursion ratio
- c) A "Cardiomyopathic differentialform" characterized by extensive diastolic abnormalities—particularly of relaxation time—already at rest
- d) A "Congestive differential form" characterized mainly by a highly increased relative A wave already at rest
- e) An "Advanced differential form" characterized by no or minimal diastolic abnormalities at rest and/or with exercise in the presence of significantly decreased left ventricular ejection fraction and/or enlarged heart The present invention also includes a characteristic parameter of early relaxation time, the ERET (=Early Relaxation Time) defined as the time interval between the onset of the aortic component of the second heart sound of phonocardiogram and the minimum of the first time derivative of the pressocardiogram (dA/dt); this time interval being used as an additional positivity criterion.

The inclusion of this new temporal parameter represents an improvement of diagnostic power of handgrip-pressocardiography independently from the mode of the use of ERET in categorization of left ventricular diastolic dysfunction based on HAT data.

It has been shown to be useful to include ERET as additional positivity criterion as follows:
ERET at rest or after exercise >20 to 60 ms, preferably >45 ms;
ERET during exercise >20 to 60 ms, preferably >45 ms. However, the upper limit of ERET is generally set by preference at 40 ms in the computer-based estimation.

In addition, the late relaxation time LARET (=LAte Relaxation Time) is calculated as a characteristic parameter; this temporal index being measured from the minimum of the dA/dt of the pressocardiographic curve to the protodiastolic nadir (O point) of this curve.

It is advantageous to correct these temporal parameters for heart rate by a modified Bazett formula resulting in the following new indexes: The early relaxation time index ERETI, given by the formula:

$$ERETI = \sqrt{A2-C}/ERET$$

Where ERET is the time from the begin of the aortic component of the second heart sound to the minimum of the time derivative of pressocardiographic curve dA/dt and A2–C the duration of diastole from the A2 to the point C of onset of systolic upstroke of pressocardiographic curve.

In addition, the late relaxation time index LARETI will be calculated in a similar way as following:

$$LARETI = \sqrt{A2-C}/LARET$$

Whereby LARET is the time interval from the minimum of dA/dt of the pressocardiogram to the protodiastolic nadir—O point—of the pressocardiographic curve, A2 the onset of second heart sound and C the onset of the systolic upstroke of pressocardiogram.

A further advantage of development of the present invention consists in a portable and handheld instrumentation—at best in pocket size—which includes the appropriate computer-based automation of HAT criteria and categories enabling us to evaluate a patient not only in a hospital, but also at the office or in sports centers and even at his home.

More advantages of the developments in the present invention are given in the claims.

Thus, the result of the present invention is an user friendly small (even pocket sized) system which does not require expertise physicians and can be executed even by personnel which are not highly skilled and can be applied in almost every patient (including disabled and elderly) and everywhere (even at patient's home) providing useful information about diastolic left ventricular function changes at rest and during isometric exercise.

This system is highly automated and can be used widely in the routine clinical practice as initial screening tool for early detection and evaluation of unknown-subclinic or known myocardial disease states including coronary artery disease; above it can be applied at every practitioner's office and in outpatient clinics well as in sports centers. Further, the application of this method by such an instrument in daily practice represents a particularly cost-effective as well as safe and convenient diagnostic modality for every patient.

BRIEF DESCRIPTION OF THE DRAWINGS

The following drawings and description of the illustrated embodiment discloses a preferred construction of the present invention in which the above advantages and features will be readily understood.

In the drawings.

DETAILED DESCRIPTION OF THE INVENTION

Figure 1:
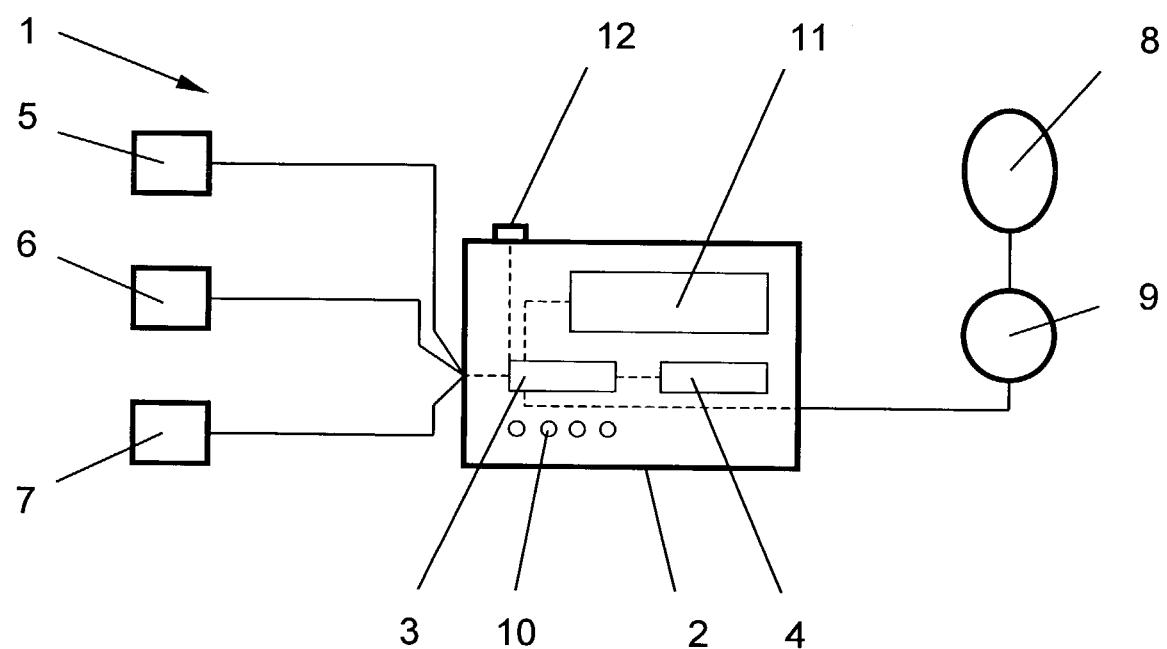
FIG. 1 is a block diagram of the diagnostic instrument illustrating the basic components of the present invention for calculating and automated evaluation of parameters of the diastolic function of the left ventricle

FIG. 1 shows a graphic illustration of an apparatus 1 for Handgrip-pressocardiographic test analysis and particularly for determining and calculating parameters of diastolic function of the left ventricle comprising a casing 2 which includes a control device 3 and interpretation unit 4. Further, casing 2 is connected to the following pick up units: the pressure transducer 5 for obtaining a tracing which mirrors left ventricular pressure, the heart sounds (phono) microphone 6 for recording the second heart sound and an electrical recorder 7 for recording ECG. Apparatus 1 includes also a device 8 for allowing the patient to perform an isometric exercise.

Control device 3 controls detection and processing of the parameters measured and data output; it also includes a programm for guiding a user. The interpretation unit 4 is connected with or implemented in control device 3. Both form an external utilization unit which determines and calculates characteristic diastolic parameters derived from a pressocardiographic curve and a phonocardiogram at rest, during and after exercise. The interpretation unit 4 converts each pressocardiogram into a digital waveform in the time domain and automatically categorizes the data measured based on categorization criteria stored in the device 1. Storage means store the data from the pressure sensor 5, microphone 6 and electrical recorder 7 during measurement over a predetermined interval.

The non-invasively obtained pressure curves at rest and during isometric handgrip-exercise are termed Handgrip-pressocardiographic Test (=HAT). Using the signal processor of the interpretation unit 4 the diastolic parameters, which will be more fully described hereinafter, will be estimated in all three steps of exercise (rest, during and after exercise). This isometric exercise is preferably performed manually with the one hand, which can be applied to assess the behavior of diastolic parameters with exercise.

Alternatively, whereas dynamic exercise could also be used using pressocardiographic parameters, it is less valuable for assessing the diastolic behavior of the left ventricle because of a much greater increase in heart rate resulting in a fusion of the diastolic waves.

Figure 5:
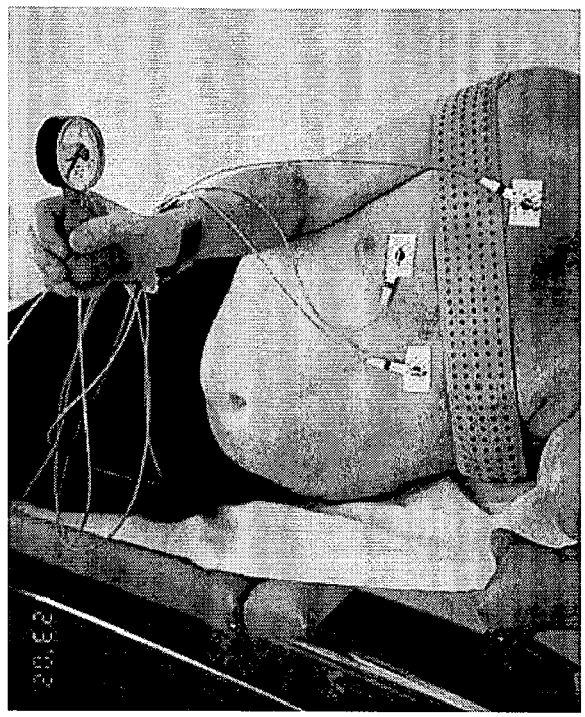
FIG. 5 shows the position of the patient and the mode of applying of the parts of the instrument for obtaining pressocardiographic tracings and performing the isometric exercise
Figure 6:
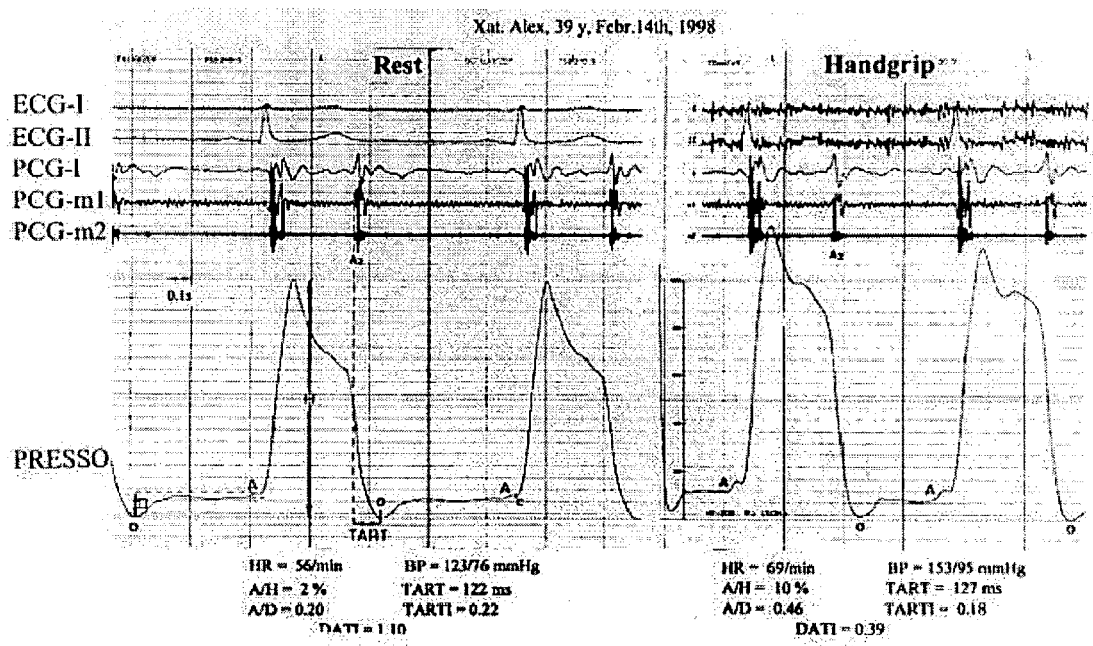
FIG. 6 shows typical pressocardiographic curves at rest (left panel) and during isometric exercise (right panel) of a patient who has no heart disease and a normal diastolic function of the left ventricle.

The non-invasively external pressure sensor 5 is placed on the thoracic wall of the patient over the site of maximal impulse of the heart beat being fixed on the thorax using an elastic strap (FIG. 5). The pressure sensor 5 should have a time constant of at least 1 sec; however, it should be preferred a time constant >3 sec and at best an infinite time constant being similar to the invasively used microtipmanometer. Using these physically correct pressure transducers, one can record high-fidelity tracings, i.e. without distortions in time and amplitude of the tracings. The sensor is connected to a preamplifier which increases the signal level. The amplified signals are filtered and transmitted to a data acquisition module in which the individual signals are converted in digital format in an already known mode. An example of a similar signal processing system to process the digitized waveform is described in the DE 197 40 931 C2; a part of this material is clearly included in the present invention.

The first time derivative dA/dt of the pressocardiographic curve will be simultaneously obtained either automated or manually calculated from the primary pressure curve. The time constant of the computer for calculating dA/dt was 0.8–1.3 ms.

Furthermore, simultaneously with the pressure transducer, a separate microphone will also be fixed 5–10 cm medial of the point of the pressure transducer; the former being also fixed on the thorax using the same or a separate elastic strap. This microphone 6 is used for recording the heart sounds and particularly a) the onset of the aortic component of the second heart sound for assessing the relaxation temporal parameters, and b) the changes of the atrial or fourth heart sound (S4) with exercise.

Figure 2:
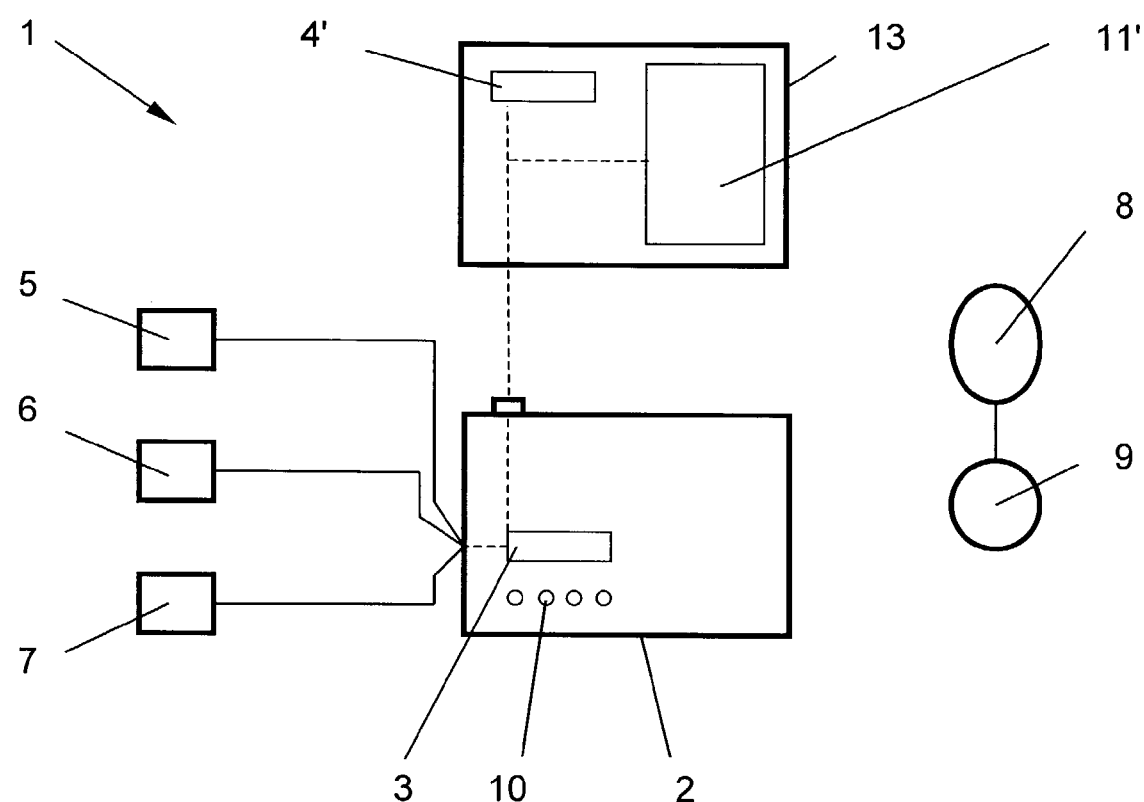
FIG. 2 is a block diagram demonstrating an alternative example of this system illustrating components of the instrumentation an embodiment of the present invention.

The manually used device 8 for performing the isometric exercise is a balloon manometer 9 with a suitable display unit for visualization of the level of the exerted pressure. The HAT examination is performed with the patient lying on the bed in the left lateral decubitus position and at the end of normal expiration without closing his mouth (for avoiding Valsalva)—as shown in FIG. 5—although technically satisfactory tracings were occasionally obtained in the supine position or during quiet breathing or both; whereas he is advised to squeeze the balloon with the one or both hands at 40% of his maximal voluntary contraction and sustaining his grip for 2 min. The pressure level is displayed in 9 which is connected to 3, whereas the level of exerted pressure can be regulated by automated signal processor. The pressure within the balloon ranged in most subjects between 0.20 and 0.50 kg/cm². It has been shown that the sustained handgrip on this lower level is sufficient enough for producing cardiac function changes, above in pressure and pressocardiographic function parameters in early and/or late diastole. As variation of this procedure using a balloon dynamometer, several other devices may be used for performing isometric exercise and alternative signal processing systems, e.g. a separated use of balloon dynamometer and the regulator 3 (FIG. 2).

Figure 3:
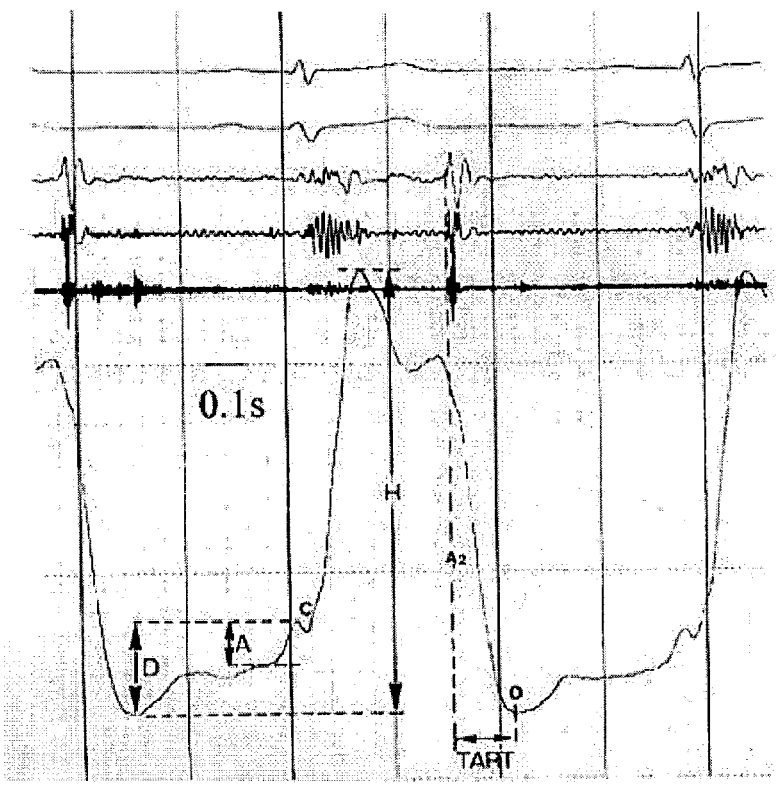
FIG. 3 is a graphical illustration of the typical curve which can be recorded using the device of the present invention which demonstrates the mode of measurement of the diastolic parameters.

At rest and during the entire duration of—particularly at 30 sec, 60 sec, 90 sec and 120 sec—as well as after isometric exercise, pressocardiograms and the phonocardiographic as well as eventually ECG tracings are when created outputted to a suitable display which may be a screen and/or a printed display (FIG. 3). Since the level of isometric stress to the heart is low, no advance events or complications like serious arrhythmias, myocardial infarctions or deaths have been hitherto reported; this representing a great advantage compared to other modes of stress testing like dynamic or pharmacological stress.

For the purpose of operation, the apparatus 1 comprises input devices 10 and a display device 11 provided on the casing 2 for monitoring a stress test. The display device 11 may also show the parameters measured and may, in the event of positivity criteria or an automatic classification or a differential diagnosis, issue a corresponding message. The casing 2 further comprises a data interface 12 for connection with a handheld computer, notebook computer or PC or a printer in order to transmit parameters measured, diagrams, error messages, etc. In a modification of the preferred embodiment the control device 3 and/or interpretation unit 4 is an external computer. Thus, it would be possible to use the apparatus 1 only for collecting data whereas interpretation is performed later. It is also possible to integrate all three units in a pocket device, e.g. a PDA.

Preferably, the casing 2 is a handheld portable unit which forms together with the sensors 5, 6 and 7 and the exercise device 8 an independent measuring apparatus.

The second embodiment shows another configuration of an apparatus 1, wherein the control device 3 is arranged in the casing 2 and the interpretation device 4' is an external computer 13 which is connected with an external display device 11'.

Figure 4:
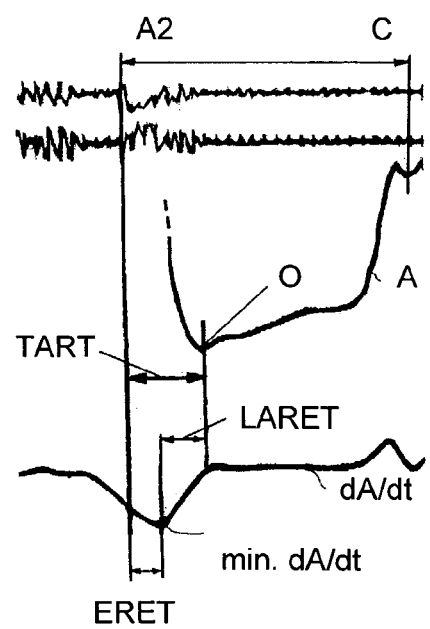
FIG. 4 is a graphical illustration of the first time derivative of the pressocardiographic curve showing the mode of measurement of the early and late relaxation parameters

In the following, the automated estimation and evaluation of the waveforms by apparatus 1 will be described in detail. FIG. 3 shows the received signals, namely the pressocardiogram ACG (in the following figures called PRESSO) which represents the time course of pressure curve changes, multiple tracings of phonocardiograms showing the heart sounds and two electrocardiograms ECG. FIG. 4 shows additionally the first time derivative of the pressocardiographic curve dA/dt.

The various variables and points used for estimating the diastolic parameters, are defined as follows:

| | |
|---|---|
| A | is the height of the A wave of the pressocardiogram ACG; whereas the point of the begin of this wave represents the most abrupt turning point in the diastolic pressocardiographic which occurs during or immediately after the end of the P wave in ECG and can also be determined using the dA/dt; |
| A2 | the onset of the aortic component of the second heart sound in the phonocardiogram PCG; |
| C | the onset of the systolic upstroke of the pressocardiogram ACG |
| D | the diastolic amplitude of the pressocardio graphic curve ACG |
| H | the total (systolic and diastolic) amplitude of the pressocardiogram ACG |
| O | the early diastolic nadir ("O point") of the pressocardiographic curve ACG; |
| TART | the total pressocardiographic relaxation time measured from the onset of the aortic component of the second heart sound A2 to the protodiastolic nadir (O point) of pressocardiogram ACG; |
| ERET | the early relaxation time which is measured from the onset of the aortic component of the second heart sound A2 to the following minimum of dA/dt of the pressocardiogram ACG; |
| LARET | the late relaxation time which is from the onset of the aortic component of the minimum of dA/dt of the protodiastolic nadir (O point) of pressocardiogram ACG. |

These variables will be estimated either by manual point identification with subsequent automated calculation or using signal processing algorithms. The computer-based automation is producing semi-automatic estimation of the following absolute and/or relative temporal and amplitude parameters:

The ratio A/H;
The ratio A/D;
The total pressocardiographic relaxation time TART;
The total pressocardiographic relaxation time index TARTI given by the formula TARTI=$\sqrt{A2-C}$/TART
The Diastolic Amplitude Time Index DATI given by the formula DATI=TARTI/(A/D);
The Early pressocardiographic Relaxation Time ERET;
The Early pressocardiographic Relaxation Time Index ERETI given by the formula ERETI=$\sqrt{A2-C}$/ERET;
The Late pressocardiographic Relaxation Time LARET;
The Late pressocardiographic Relaxation Time Index LARETI given by the formula LARETI=$\sqrt{A2-C}$/LARET.

In the signal processor for estimating the diastolic parameters 4 of the device 1, the following positivity criteria are included:

TART at rest or after exercise >159 ms;
TART during exercise >155 ms;
TARTI at rest or after exercise <0.16;
TARTI during exercise <0.14 or preferred <0.12;
A/H at rest or after exercise >0.22;
A/H during exercise >0.22;
DATI at rest or after exercise <0.20;
DATI during exercise <0.20;
ERET at rest or after exercise >0.45 ms;
ERET during exercise >45 ms.

However, one can also choose slightly different critical values from these above given limits; whereas a deviation of these limits of 10 to 15% in both directions of each critical value can be tolerated.

In the signal processor of the interpretation unit 4, there is categorization for example of diastolic differential forms being defined partly by use of the mentioned characteristic parameters. Based on the exactly defined limits as well as on some characteristic forms of behavior of the mentioned positivity criteria with exercise, an automated categorization results by proper selection of the most similar diastolic differentialform; this can be outputted to a suitable display which may be a screen 11 or a printed display.

Using the instrument with the programmed processing unit 4, an automated categorization can be based on the critical values of mentioned parameters and the direction or magnitude of changes with exercise; thus, establishing a basis for accurate comparison of each patient's data with a known class of patients, whereas a direct status output is produced. The categorization criteria are included in the interpretation unit 4. The mode of discrimination and subsequent classification is as follows:
 a) Classification of patients with a positive/abnormal or negative/normal test result according to the presence or not of exactly defined critical limits of some temporal and relative A wave amplitude parameters;
 b) Classification according to the severity of diastolic dysfunction;
 c) Classification according to early or late diastolic dysfunction;
 d) Classification according to ischemic or non-ischemic diastolic response to exercise.

The criteria of differentialform categorization are defined according to absolute values and/or magnitude of exercise-induced changes, as it will be analyzed hereinafter. Using this automated categorization, the analysis of the results does not require an operator with a skill above clerical personnel in order to potentially diagnose the underlying myocardial disease state.

The utilization is based initially in the presence or absence of critical values of characteristic parameters, and subsequently the discrimination of types (relaxation and/or compliance) and of severity of diastolic dysfunction (slight, moderate or severe). An additional categorization consists in discriminating an ischemic from a non-ischemic response.

By the present invention, there is an improved final evaluation by the direct status output consisting in less "false-positive" test results as well as in a significantly improved discrimination ability of type and severity of myocardial dysfunction in each case as well as diagnosis of underlying myocardial disease. At best a portable small— even pocket sized—instrument is used for an automated rapid categorization of patients.

Category I: Characteristic Parameter

A pressocardiographic test result will be defined as positive or abnormal or pathologic, when at least one of said characteristic parameters is higher than the mentioned upper limit or lower than the lowest normal limits; alternatively, a positive result is given by the presence of one of the following types of diastolic dysfunction.

Category II: Types of Left Ventricular Diastolic Dysfunction
 1. Compliance type of diastolic dysfunction (C-type)
  A Compliance type is defined by the presence of an A/H>0.22 before and/or during and/or after the exercise.
 2. Relaxation type of diastolic dysfunction (R-type)
  A Relaxation type is defined by the presence of an abnormal absolute (TART) and/or relative (TARTI) prolongation of the total relaxation time at rest and/or during and/or after exercise (FIG. 7)
  At rest: prolongation of TART>159 ms or decrease of TARTI<0.16.
  During and/or after exercise: TART>155 ms and/or TARTI<0.14; when the heart rate is >80 bpm the limit for TARTI should be <0.12
 3. Mixed type of diastolic dysfunction (RC-type)
  A mixed type is defined by the presence before and/or during and/or after isometric exercise of both a C- and a R-type in the same heart beat (FIGS. 8–11).
 4. DATI type (DATI-type) of slight diastolic dysfunction
  A DATI type is defined by the absence of all mentioned 3 diastolic types and by the isolated presence of an abnormal DATI (=DATI<0.20) at rest, during or after exercise Category III: Discrimination of Severity of Left Ventricular Diastolic Dysfunction In the presence of a positive HAT result, the following definition of level of abnormal values of parameters is given at rest and/or during and/or after exercise:
 1. Slight diastolic dysfunction (FIGS. 7 and 8): TART<185 ms and A/H<0.35 and/or DATI<0.20
 2. Moderate diastolic dysfunction: TART>185 ms and <210 ms and/or A/H>0.35 and <0.41
 3. Severe diastolic dysfunction (FIGS. 9–11): TART>210 ms and/or A/H>0.41

Category IV: Ischemic and Non-ischemic Diastolic Response

Abnormal/pathologic/positive test results can show an ischemic and those with a non-ischemic response. The presence of an ischemic diastolic response or ischemic pattern is given by the presence of the following abnormalities:

Depending on the presence of a C- or R- types, one can discriminate between an ischemic diastolic response of C-, RC-, or R-type. It should be noted that depending on which of these types is present, the lowest value of relaxation or A wave parameters at rest or during or after exercise will be taken as baseline critical value for estimating the magnitude of change between the phases of exercise test in percentage of the baseline value; the following comparisons will be made: rest vs after exercise, rest vs during exercise and after exercise vs during exercise.
 1. C-ischemic
 This pattern is present only in cases that all relaxation parameters in all phases of exercise are within normal limits; in addition, the following alterations in end-diastole should be present:
  A) A/H at rest or after exercise within normal limits (<0.22); whereas an abnormal A/H (>0.22) value is reached early and/or continuously and/or gradually during or after exercise from 60 to >200%, preferably 75% of baseline A/H value. This behavior of A/H can also be termed "ischemic end-diastolic rise".
  B) A/H is already at rest abnormal (>0.22); there is a further increase in A/H during and/or after exercise, whereas the lowest value at rest or after exercise will be taken as the baseline value and the value during or after exercise as the final value.

These changes of A/H can be defined to be of ischemic origin only if its maximal value reached in at least one of the phases of exercise is abnormal (>0.22); whereas the definition of percentage increase in A/H which is defined as ischemic, depends on the range of maximal value of A/H which will be taken as baseline value as follows:
 1. When baseline A/H=0.22 to 0.30, a rise from 40 to 60%, preferably >50% of baseline value;
 2. When baseline A/H=0.31 to 0.41, a rise from 30 to 40%, preferably >30% of baseline value;

3. When baseline A/H is >0.41, a rise from 10 to 30%, preferably >20% of baseline value.

2. R-ischemic

This pattern of response is defined by the absence of an abnormal A/H value in all phases of test; additionally, the following magnitude of changes in relaxation changes should be present: the baseline value (i.e. at rest or after exercise) of TART or TARTI is within normal limits or abnormal, there is a prolongation of TART of >22% and a decrease of TARTI>0.02 compared to the baseline value; both parameters being abnormal.

3. RC-ischemic

As an ischemic mixed pattern, we define the simultaneous occurrence in the same heart beat of both the R-ischemic and the C-ischemic responses.

It should be emphasized, therefore, that in order to categorize a test result as ischemic diastolic response or ischemic pattern, the maximal magnitude of changes in A/H and/or TART and TARTI among the three phases of exercise should be considered, i.e. the maximal change between rest vs exercise or rest vs after exercise or exercise vs after exercise.

Category V: Diastolic Forms or Differentialforms

Figure 7:
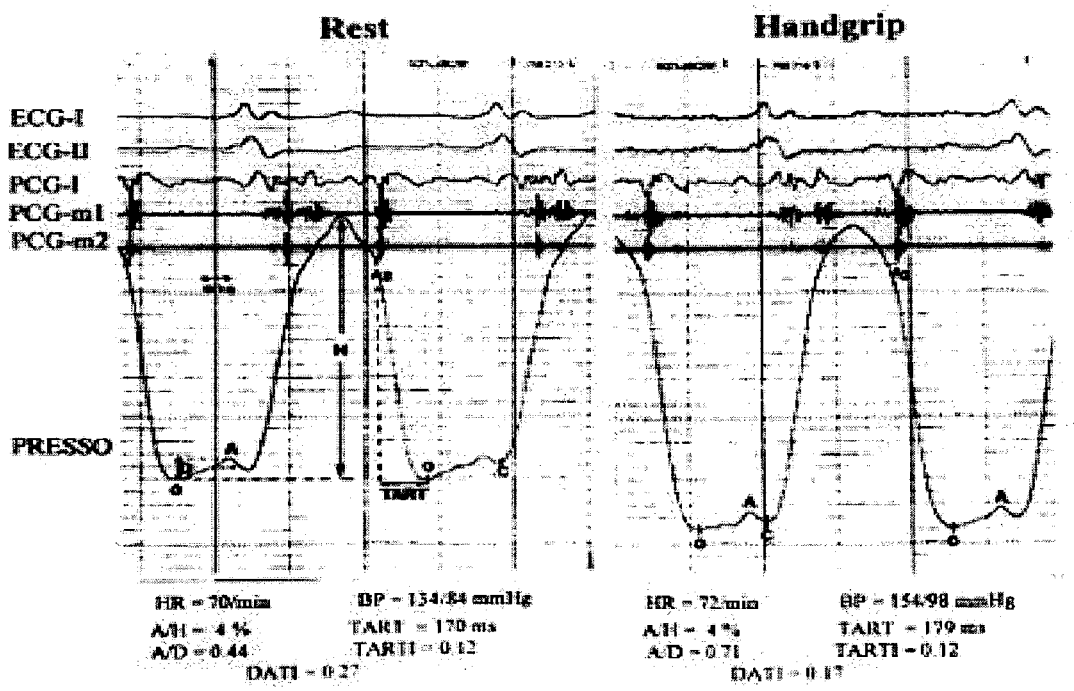
FIG. 7 shows pressocardiograms at rest (left panel) and during isometric exercise (right panel) of a second patient with chronic arterial hypertension

Based on combined exact definitions, the following five categories of diastolic forms of cardiac performance alterations with isometric exercise can be estimated by a computer-based automation and a "diastolic form" recognition algorithm that converts the parameters into a substantial and reliable estimate of cardiac performance behavior with exercise; whereas the diagnosis of underlying myocardial disease by use of a proper algorithm is given in a robust manner. These diastolic or differential forms are exactly defined as following:

1. Diastolic Hypertensive Form or Differentialform (FIG. 7)

Figure 8:
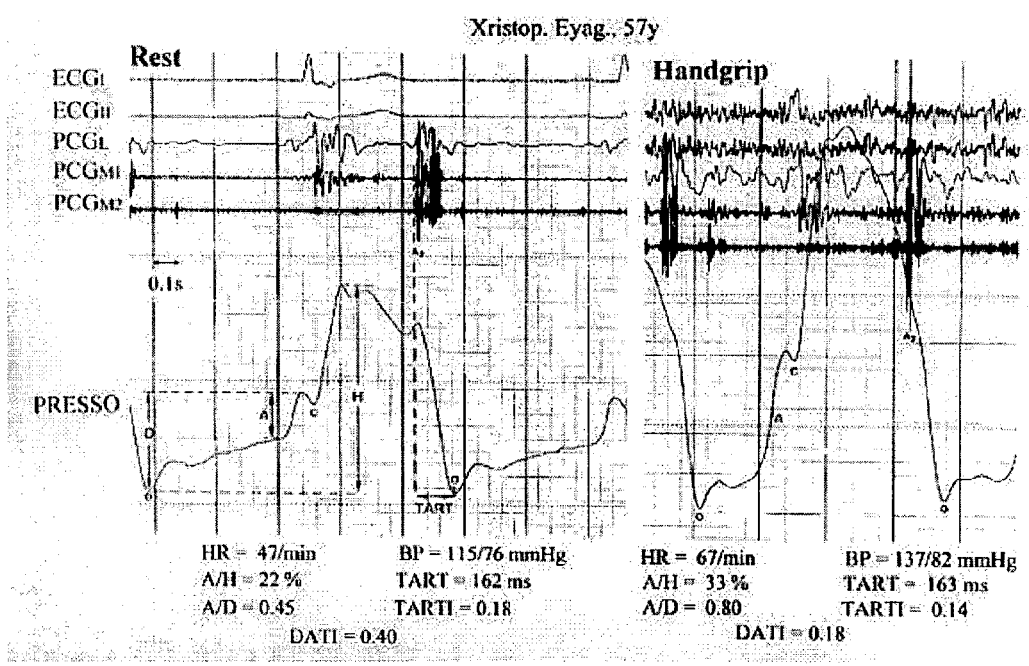
FIG. 8 shows pressocardiograms at rest (left panel) and during isometric exercise (right panel) of a third patient with coronary artetry disease

This diastolic form is characterized by the following abnormal changes in the left ventricular function in diastole as assessed by use of pressocardiogram: At rest, there is a slight to moderate alteration of TART (159 ms to 210 ms) and/or an only slightly increased A/H (0.21 to 0.35) and a slight decrease in DAT (0.20–0.16). During and/or after isometric exercise, only slight additional changes (no moderate or above severe diastolic dysfunction as in III.2 and III.3) are occurring. Thus, a hypertensive form is defined by the presence of the following criteria:
  a) A mostly slight diastolic dysfunction at rest, during and after exercise, as defined in III.1
  b) Absent deterioration of type in the course of exercise phases (rest→exercise→after exercise), i.e. no transition in these phases from R-type (II.2) to RC-type (II.3) and to C-type (II.1); instead it occurs either no change or an improvement of type from rest to exercise and after exercise, i.e. a transition from C-type to RC-type and to R-type.
  c) Non-ischemic diastolic response 2. Diastolic Coronary Form or Differentialform (FIG. 8)

Figure 9:
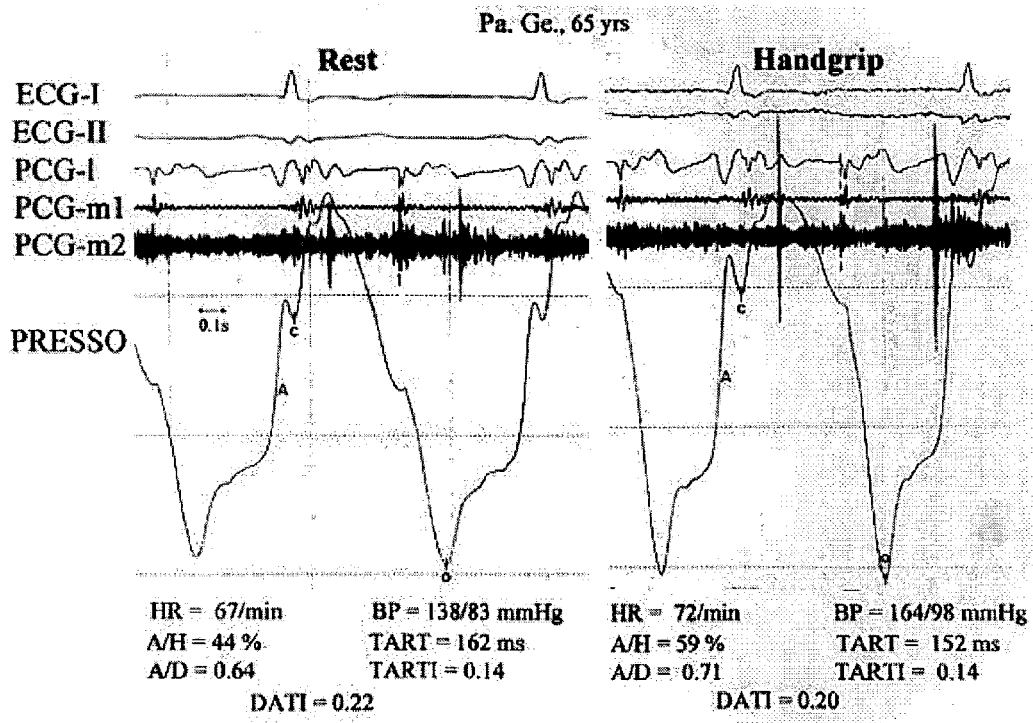
FIG. 9 shows pressocardiograms at rest (left panel) and during isometric exercise (right panel) of a fourth patient with unstable angina pectoris

The diastolic coronary form is characterized by the presence of the following abnormal changes of diastolic left ventricular function as assessed by the pressocardiogram: In the chronic phase of coronary artery disease, i.e. in absence of symptoms or other signs of acute coronary syndrome, there is at rest, a normal or slight to moderate diastolic dysfunction as defined in III.1 or III.2 (FIG. 8). In the acute or subacute phase of coronary heart disease, there is at rest often a severe diastolic dysfunction of the left ventricle; in this case the criteria which are described in IV.1.b (FIG. 9).

During and after isometric exercise, an often dramatic alteration in diastole occurs with simultaneous deterioration of type from rest to exercise, the onset of which occurs often very early (i.e. within the initial 15 sec to 30 sec of exercise); these alterations show mostly either a progression or a changing pattern with or after exercise. Typically, the A/H increases>0.30 and TART>180 ms. The coronary differentialform is, thus, defined by the presence of at least two of the following three criteria:
  a) Deterioration of type
  b) Ischemic diastolic response
  c) TART>180 ms and/or A/H>0.30

Figure 10:
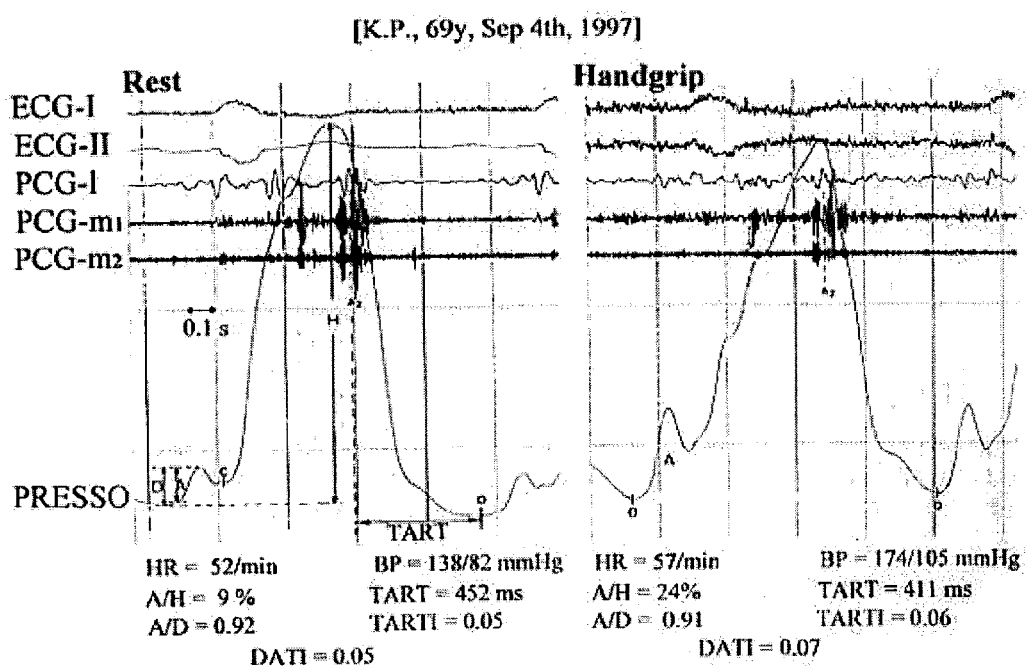
FIG. 10 shows pressocardiograms at rest (left panel) and during isometric exercise (right panel) of a fifth patient with non-obstructive cardiomyopathy

3. Diastolic Cardiomyopathic Form or Differentialform (FIG. 10)

The diastolic Cardiomyopathic form is characterized by the occurrence of the following abnormal alterations in the diastolic ventricular function in diastole as assessed by means of pressocardiogram:

At rest, there is a extreme prolongation of TART (>210 ms) or a extensive decrease in TARTI (<0.10) and/or a moderate to severe increase in A/H (>0.35 or >0.41).

During or after exercise TART shortens and/or A/H increases.

Figure 11:
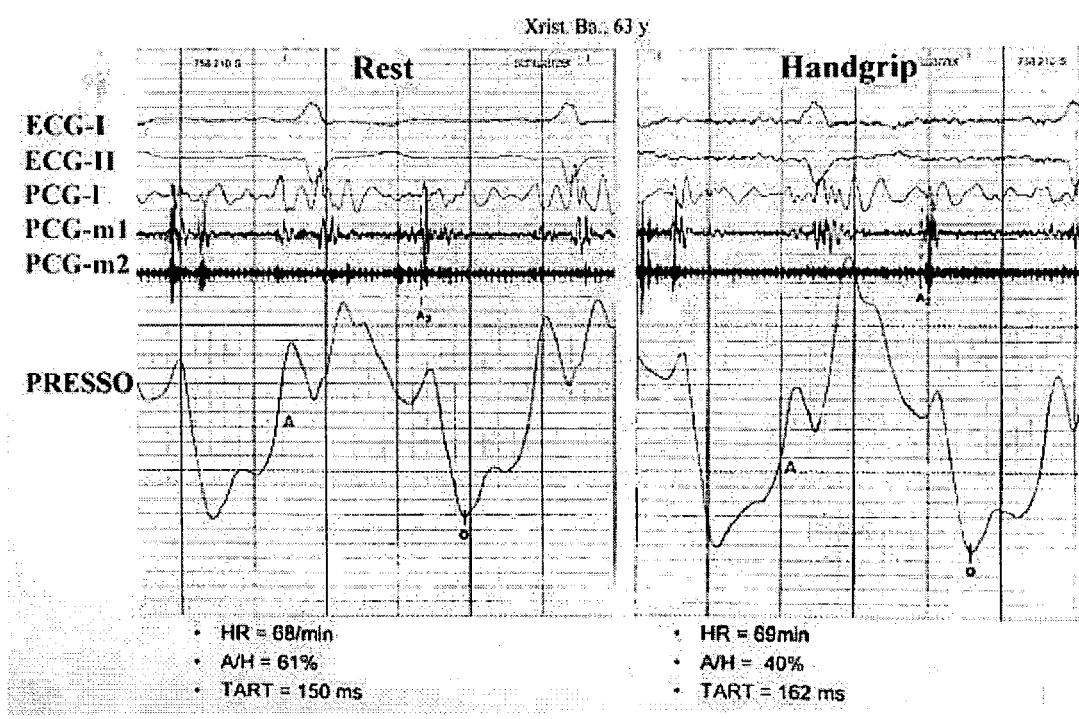
FIG. 11 shows pressocardiograms at rest (left panel) and during isometric exercise (right panel) of a sixth patient with congestive heart failure

A diastolic cardiomyopathic form is, thus, defined by the presence of the following tree criteria:
  a) Moderate to severe diastolic dysfunction at rest, during and after isometric exercise (II.2 or III.3); especially an extreme prolongation of TRAT>210 ms already at rest.
  b) No deterioration of type in the phases of exercise
  c) Non-ischemic reaction 4. Diastolic Congestive Form or Differentialform (FIG. 11)

The diastolic congestive form is characterized by the following abnormal alterations of left ventricular function in diastole as assessed by the pressocardiogram:

At rest, the A/H shows a moderate to severe increase (>0.35), whereas—in contrast to the cardiomyopathic differentialform—TART and TARTI show an only slight to moderate increase and decrease, respectively.

During and after exercise, there are only slight additional changes, i.e. A/H increases and/or TART decreases slightly.

A congestive differentialform is, thus, defined by the presence of all following criteria:
  a) Moderate to severe C-type (II.1 and III.2 or III.3) already at rest
  b) Non-ischemic diastolic response
  c) No change in type (neither deterioration nor improvement) in all 3 phases of exercise 5. Diastolic Advanced Form or Differentialform This diastolic advanced form occurs in the presence of systolic left ventricular dysfunction and/or clearly dilated left heart. This differentialform is defined further by the presence of the following abnormal alterations in diastolic left ventricular function, as assessed by means of pressocardiogram:

At rest, there are no or only minimal diastolic abnormalities (C-, R- or RC-type). During and after isometric exercise, there are no or only minimal changes from baseline. Thus, an advanced differentialform is defined by the presence of all following criteria:
  a) Dilated left ventricle and/or systolic dysfunction of the left ventricle as assessed by angiography and/pr echocardiography and/or an other imaging technique.
  b) Non-ischemic diastolic response
  c) No change in type during the three phases of exercise.

The application of the described and analyzed new definitions of positivity criteria, types, patterns of response and differentialforms of abnormal alterations in pressocardiographic curve at rest, during and after isometric exercise, reflect a sensitive marker of analogous pressure changes within the left ventricle; thus, representing a novel opportunity to assess cardiac diastolic performance and detect potentially life-threatening abnormal heart conditions using an operator with minimal medical skills. The low level isometric exercise test of very short duration represents an easily and conveniently applied new simple noninvasive technique with no requirement of skilled interpretation because after an easy identification of some marked points on the pressocardiographic curve, an automated evaluation of the result (positive/negative, C-, R- and RC-types, Ischemic/Non-ischemic, and Hypertensive vs Cardiomyopathic vs Coronary vs Congestive vs Advanced differentialforms) is provided by use for example of instrumentation 1.

This instrument can be portable and small—even in pocket size, whereas a laptop or PDA can be used.

Alternatively, it should be emphasized, again, that current noninvasive diagnostic methods are either not sensitive enough (rest-ECG and rest-echocardiography) or too complicated and/or time-consuming and/or very costly and require expert interpretation; therefore, most of these methods can not be used efficiently as daily used simple screening tools by every primary care physician. In this context, it should be mentioned that asymptomatic patients are usually not coming to the great hospitals or to the office of cardiologists in order to be examined by more sophisticated techniques. Therefore, they could be almost exclusively identified in the primary care (GPs or Internists etc).

It should be realized that there are almost no simple, rapid and cost-effective diagnostic methods for wide application as initial screening tools for detecting early "silent" myocardial disease states—and particularly coronary artery disease. The inventor has realized that the handgrip-pressocardiography can be helpful in solving this great health care problem when applied widely.

Given the continuing emphasis on cost and productivity of screening methods and instruments for a clinical wide application and early cardiac evaluation, this diastolic stress test by use of handgrip-pressocardiography represents a highly sensitive and specific novel diagnostic modality for separating healthy subjects from asymptomatic myocardial disease patients (including above those with silent coronary artery disease or cardiomyopathy) helping, in addition, significantly in differentiating among patients with various myocardial disease states. Particularly, the differentiation of patients in some diagnostic "gray zones" in cardiology would be facilitated: hypertensive vs cardiomyopathy, athlete's heart vs early or atypical cardiomyopathy, coronary vs congestive heart failure etc.

In addition, due to its safety and short duration and low level of exercise, this diastolic stress test can be obtained everywhere by a portable device—even at patient's home—and also in disabled or elderly persons, who can mostly not perform dynamic or other stress tests.

Further, it is expected that the handgrip-pressocardiographic test could have a much wider spectrum of applications using also quite different devices than mentioned in the present claims of invention.

I claim:

1. A method of rapid noninvasive measurement of parameters of diastolic function of left ventricle and automated evaluation of the measured profile of left ventricular function at rest and with exercise, wherein:

the patient performs an isometric exercise trough an external device, an external pressure transducer and heart sounds microphone are applied as noninvasive sensor units on the thoracic wall to obtain a noninvasive left ventricular pressure mirroring curve and simultaneously the heart sounds; and and an external utilization unit determines and calculates characteristic diastolic parameters derived from the pressocardiographic curve and phonocardiogram at rest, during and after exercise, converts each said pressocardiogram into a digital waveform in the time domain, and automatically categorizes the mentioned characteristic parameters based on exact categorization criteria for defining at least one of the following differentialforms of diastolic dysfunction of left ventricle in human beings:

a) a diastolic Hypertensive differential form
b) a diastolic Coronary differential form
c) diastolic Cardiomyopathic differential form
d) a diastolic Congestive differential form
e) a diastolic Advanced differential form.

2. The method of claim 1 including estimation of the following selected parameters and based on which the following categories are defined:

a) Distinction whether at least one of diastolic characteristic parameters, shows a critical value within defined limits of abnormality; this representing an abnormal-pathologic finding;
b) Distinction according to the severity of diastolic alterations
c) Discrimination between early and late diastolic abnormalities
d) Discrimination of an ischemic from non-ischemic diastolic response or pattern;

wherein the definition of differentialform-categorization criteria is based on a selection and combination of the said discrimination criteria.

3. The method of claim 2 wherein said severity of diastolic alterations is slight, moderate and severe output.

4. The method of claim 2 wherein said discrimination of early from late diastolic abnormalities is the following:

a) An early diastolic abnormality;
b) A late diastolic abnormality; and
c) A combined diastolic abnormality, whereas early and late diastolic abnormalities are simultaneously present in the same heart beat.

5. The method of claim 2 wherein said diastolic ischemic and non-ischemic patterns or reactions are separated by comparing the absolute values as well as the pattern and magnitude of changes among the three steps of exercise testing as follows:

a) An ischemic diastolic reaction or pattern, being defined by an abnormal increase in relative A wave to total excursion H, of said pressocardiographic curve from 15 to 100%, preferably 20 to 75% of the baseline value or/and an abnormal prolongation of absolute or relative relaxation time; and
b) A non-ischemic diastolic reaction or pattern, being defined by an abnormal result in the absence of the mentioned ischemic diastolic reaction.

6. The method of claim 1 wherein said characteristic parameter comprises one of the early relaxation time ERET as the time interval between onset of the aortic component A2 of the second heart sound in said phonocardiogram and the following minimum of the first time derivative dA/dt of said pressocardiographic curve; and the late relaxation time LARET as the time interval between said minimum of the first time derivative dA/dt and the protodiastolic nadir of pressocardiographic curve; and the early relaxation time index ERETI=√A2−C/ERET where said ERET is the time interval between said aortic component A2 of the second heart sound in the phonocardiogram and the following said minimum of the first time derivative dA/dt of the pressocardiographic curve and C the onset of the systolic upstroke of the pressocardiographic curve; and the late relaxation time index LARETI=√A2−C/LARET where said LARET is the time interval between said minimum of first time derivative dA/dt of the pressocardiographic curve and the O point of pressocardiographic curve, A2 the onset of the aortic component of the second heart sound in phonocardiogram and C the onset of systolic upstroke of the pressocardiogram, and/or the ratio A/H being the relative height of said A wave to said total height of pressocardiographic curve; and the total pressocardiographic relaxation time TART from said onset of second heart sound A2 to said protodiastolic nadir of pressocardiogram; and/or heart rate corrected relaxation time index TARTI is calculated as follows: TARTI=√A2−C/TART, where said A2 is the onset of second heart sound in phonocardiogram and C is the begin of systolic upstroke of pressocardiogram; and the combined relaxation and A wave parameter DATI which is calculated as follows: DATI=TARTI/(A/D) where A is the height of the A wave and D the diastolic amplitude of pressocardiographic curve.

7. The method of claim 6 wherein said early relaxation time ERET is a positivity criterion of EAT with the following upper normal limits:
ERET at rest or after exercise >20 to 60 ms, preferably >45 ms;
ERET during exercise >20 to 60 ms, preferably >45 ms.

8. The method of claim 6 wherein said characteristic parameter A/H is taken as a positivity criterion of HAT with the following upper normal limits:
A/H at rest or after exercise >0.16 to 0.26, preferably >0.22;
A/H during exercise >0.16 to 0.26, preferably >0.22.

9. The method of claim wherein said characteristic parameter TART will be included as a positivity criterion of HAT having the following upper normal limits:
TART at rest or after exercise >140 ms to 1=ms, preferably 159 ms;
TART during exercise >140 ms to 159 ms, preferably >155 ms.

10. The method of claim 6 wherein said characteristic parameter TART as positivity criterion is defined as follows:
TARTI at rest or after exercise <0.17 to 0.14, preferably <0.16;
TARTI dining exercise <0.17 to 0.14, preferably <0.14 or when heart rate >80 bpm preferably <0.12.

11. The method of claim 6 wherein said characteristic parameter DATI is included as positivity criterion of HAT and its lowest normal limits are defined as follows:
DATI at rest or after exercise <0.26 to 0.17, preferably <0.20;
DATI during exercise <0.26 to 0.17, preferably <0.20.

12. The method of claim 6 wherein said severity of diastolic dysfunction of the left ventricle as assessed by said pressocardiographic parameters, is defined as slight, moderate and severe diastolic dysfunction occurring in at least one of the three steps of exercise test as follows:
  a) Slight dysfunction: abnormally prolonged TART<185 ms and/or abnormally increased A/H<0.35 or an isolated abnormal decrease of DATI <0.20
  b) Moderate dysfunction; TART>185 ms and/or<210 ms and/or A/H>0.35 and<0.41;
  c) Severe dysfunction: TART>210 ms and/or A/H>0.41.

13. The method of one claim 6 wherein said ischemic diastolic reaction or pattern is including three categories being defined as follows:
  A) The C-ischemic reaction, which is characterized as follows:
    1. A/H at rest or after exercise within normal limits; whereas during or after exercise, it occurs an abnormal and early and/or continuous and/or gradual increase A/H from 60 to >200%, preferably 75% of baseline value;
    2. A/H is already at rest abnormal; there is a further increase in A/H during and/or after exercise, whereas the lowest value at rest or after exercise will be taken as the baseline value and the value during or alter exercise as the final value; whereas the magnitude of A/H increase which is defined as ischemic depends on the level of A/H's baseline value as follows:
      when baseline A/H=0.22 to 0.30, a rise from 40 to 60%, preferably >50% of baseline value;
      when baseline A/H=0.31 to 0.41, a rise from 30 to 40%, preferably >30% of baseline value;
      when baseline A/H is >0.41, a rise from 10 to 30%, preferably >20% of baseline;
  B) The R-ischemic reaction, which is defined as follows:
    absence of an abnormal A/H value in all phases of the test;
    a prolongation of TART of>22% and a decrease of TARTI>0.02 compared to the baseline value; whereas the baseline value of TART or TARTI is within normal limits or abnormal;
  C) The RC-ischemic reaction or Mixed ischemic reaction, which is characterized by and defined as follows:
    simultaneous occurrence in the same heart beat of both the R- ischemic and the C-ischemic responses,
  wherein in A, B and C the lowest observed value of all maximal measured values at rest or after exercise is taken as the baseline value; whereas the maximal value observed during or after the exercise, is taken as the maximal value; finally, the magnitude of the difference between the maximal and baseline and maximal value with exercise, expressed as percentage of baseline value, is then used for defining an ischemic diastolic response or pattern.

14. The method of claim 6 including a signal processing and utilization unit by which the signal sequences including the automated positivity criteria are then processed in an appropriate computerized pattern recognition processing method and means for classifying of the results of series of pressocardiographic diastolic measurements to produce an output diagnosing diastolic differentialforms.

15. The method of claim 6 wherein said diastolic Hypertensive differential form is diagnosed, when the following category criteria are fulfilled:
  a) slight diastolic dysfunction at rest, dining and after exercise;
  b) absence of deterioration of type, particularly no transition in the following direction: R-type→RC-type→C-type;
  c) Non-ischemic reaction or pattern.

16. The method of claim 6 wherein said diastolic Coronary differential form is diagnosed, when at least two of the following three category criteria are fulfilled:
   a) Deterioration of diastolic type with exercise, i.e. transition in the following direction: R-type→RC-type→C-type;
   b) Ischemic reaction or pattern;
   c) TART>180 ms and/or A/H>0.30.

17. The method of claim 6 wherein said diastolic Cardiomyopathic differential form is diagnosed, when the following category criteria are fulfilled:
   a) moderate to severe diastolic dysfunction at rest and during and/or after exercise; particularly a prolongation of TART>210 ms and/or decrease in TARTI<0.10 or an increase in A/H>0.35 or>0.41;
   b) No deterioration of diastolic type, i.e. no transition in the following direction: R-type→RC-type→C-type;
   c) Non-ischemic reaction or pattern.

18. The method of claim 6 wherein said diastolic Congestive differentialform is diagnosed, when the following category criteria are fulfilled:
   a) moderate to severe C-type, particularly when present already at rest;
   b) No change in diastolic type, particularly no transition in the following direction: R-type→RC-type→C-type or an improvement in opposite direction;
   c) Non-ischemic diastolic reaction or pattern.

19. The method of claim 6 wherein the diastolic Advanced differential form is diagnosed, when the following category criteria are fulfilled:
   a) Dilated left ventricle and/or global systolic dysfunction of left ventricle as assessed e.g. by means of echocardiogram and/or angiography;
   b) Slight changes in all phases of exercise and non-ischemic diastolic reaction or pattern;
   c) No change in diastolic type in all phases of exercise, transition in the following direction: R-type→RC-type→C-type.

20. The method of claim 6 wherein said temporal and/or relative A wave amplitude and/or combined parameters of diastolic function of left ventricle as assessed by means of pressocardiography and phonocardiography are measured within the range of 60 to 240 sec of isometric exercise, preferably within the range of 120 see, and in time intervals of 30 sec to 60 sec in all phases of exercise.

21. The method of claim 6 wherein the exercise is selected to assess the level of providing a quantitation of the isometric exercise from 30 to 100% of maximum voluntary contraction.

22. The method of claim 6 including a processor utilization unit in a portable unit/box being connected to a portable light pressure transducer and small heart sounds microphone; whereas all together representing an independent autonomous system which can be produced in pocket form.

23. A device for rapid noninvasive measurement of parameters of diastolic function of left ventricle and automated evaluation of the profile of left ventricular function at rest and with exercise, comprising:
   external pressure sensor and heart sounds microphone as noninvasive sensor units applicable on the thoracic wall for obtaining a noninvasive left ventricular pressure mirroring curve and simultaneously the heart sounds;
   an external device enabling the patient to perform an isometric exercise, and
   an external utilization unit for determining and calculating of characteristic diastolic parameters derived from the pressocardiographic curve and phonocardiogram at rest, during and after exercise, converting each said pressocardiogram into a digital waveform in the time domain, and automatically categorizing based on the mentioned characteristic parameters;
   whereby the utilization unit contains exact categorization criteria for defining at least one of the following differentialforms of diastolic dysfunction of left ventricle in human beings:
      a) a diastolic Hypertensive differential form;
      b) a diastolic Coronary differential form;
      c) a diastolic Cardiomyopathic differential form;
      d) a diastolic Congestive differential form;
      e) a diastolic Advanced differential form.

24. The device of claim 23 including estimation of the following selected parameters and based on which the following categories are defined:
   a) Distinction whether at least one of diastolic characteristic parameters, shows a critical value within defined limits of abnormality; this representing an abnormal-pathologic finding;
   b) Distinction according to the severity of diastolic alterations
   c) Discrimination between early and late diastolic abnormalities
   d) Discrimination of an ischemic from non-ischemic diastolic response or pattern;
wherein the definition of differential form categorization criteria is based on a selection and combination of the said discrimination criteria.

25. The device of claim 24 wherein said severity of diastolic alterations is slight, moderate and severe output.

26. The device of claim 24 wherein said discrimination of early from late diastolic abnormalities is the following:
   a) An early diastolic abnormality
   b) A law diastolic abnormality; and
   c) A combined diastolic abnormality, whereas early and late diastolic abnormalities are simultaneously present in the same heart beat.

27. The device of claim 24 wherein said diastolic ischemic and non-ischemic patterns or reactions are separated by comparing the absolute values as well as the pattern and magnitude of changes among the three steps of exercise testing as follows:
   a) An ischemic diastolic reaction or pattern, being defined by an abnormal increase in relative A wave to total excursion H, of said pressocardiographic curve from 15 to 100%, preferably 20 to 75% of the baseline value or/and an abnormal prolongation of absolute or relative relaxation time; and
   b) A non-ischemic diastolic reaction or pattern, being defined by an abnormal result in the absence of the mentioned ischemic diastolic reaction.

28. The device of claim 24 wherein said device for performing the exercise is selected to assess the level of providing a quantitation of the isometric exercise from 30 to 100% of maximum voluntary contraction, preferably 40 to 50% of maximal leg/foot or hand contraction.

29. The device of claim 24 including a sensor unit for obtaining pressocardiograms comprising an external pressure sensor with ideally an infinite time constant -or with time constant of >3 sec for being fixed on the thoracic wall by means of an elastic strap at the point of maximal cardiac impulse.

30. The device of claim 29 wherein the sensor unit further includes a heart microphone for simultaneously obtaining of heart sound this microphone being separately placed in a place of the thoracic wall having the strongest A2 signal and being fixed also by an elastic strap on place.

31. The device of claim 30 wherein the sensor unit further includes a sensors for simultaneously obtaining of an electrocardiogram.

32. The device of claim 24 including a processor utilization unit in a portable unit being connected to a portable light pressure sensor and small heart sounds microphone, all together representing an independent autonomous system which can be produced in pocket form.

33. The device of claims 24 including a casing and a connecting point to PC, laptop, PDA or printer.

34. The device of claim 23 wherein said characteristic parameter comprises:

the early relaxation time ERET as the time interval between onset of the sortie component A2 of the second heart sound in said phonocardiogram and the following minimum of the first time derivative dA/dt of said pressocardiographic curve; and/or the late relaxation time LARET as the time interval between said minimum of the first time derivative dA/dt and the protodiastolic nadir of pressocardiographic curve; and/or the early relaxation time index ERETI=$\sqrt{A2-C}$/ERET where said ERET is the time interval between said aortic component A2 of the second heart sound in the phonocardiogram and the following said minimum of the first time derivative dA/dt of the pressocardiographic curve and C the onset of the systolic upstroke of the pressocardiographic curve; and/or the late relaxation time index LARETI=$\sqrt{A2-C}$/LARET where said LARET is the time interval between said minimum of first time derivative dA/dt of the pressocardiographic curve and the O point of pressocardiographic curve, A2 the onset of the aortic component of the second heart sound in phonocardiogram and C the onset of systolic upstroke of the pressocardiogram, and/or the ratio A/H being the relative height of said A wave to said total height of pressocardiographic curve; and/or the total pressocardiographic relaxation time TART from said onset of second heart sound A2 to said protodiastolic nadir of pressocardiogram; and/or heart rate corrected relaxation time index TARTI is calculated as follows: TARTI=$\sqrt{A2-C}$/TART, where said A2 is the onset of second heart sound in phonocardiogram and C is the begin of systolic upstroke of pressocardiogram; and/or the combined relaxation and A wave parameter DATI which is calculated as follows: DATI=TARTI/(A/D) where A is the height of the A wave and D the diastolic amplitude of pressocardiographic curve.

* * * * *